US010413446B2

(12) United States Patent
Bouch et al.

(10) Patent No.: US 10,413,446 B2
(45) Date of Patent: Sep. 17, 2019

(54) MANUFACTURING AN ARTICULATING OPHTHALMIC SURGICAL PROBE

(71) Applicant: NOVARTIS AG, Basel (CH)

(72) Inventors: Dustin J. Bouch, Newport Beach, CA (US); Raffi S. Pinedjian, Fountain Valley, CA (US); Timothy C. Ryan, Laguna Hills, CA (US)

(73) Assignee: Novartis AG, Basel (CH)

( * ) Notice: Subject to any disclaimer, the term of this patent is extended or adjusted under 35 U.S.C. 154(b) by 784 days.

(21) Appl. No.: 14/612,576

(22) Filed: Feb. 3, 2015

(65) Prior Publication Data

US 2015/0223976 A1 Aug. 13, 2015

Related U.S. Application Data

(60) Provisional application No. 61/936,434, filed on Feb. 6, 2014.

(51) Int. Cl.
*A61F 9/00* (2006.01)
*A61F 9/007* (2006.01)
*A61B 90/30* (2016.01)
*A61B 1/005* (2006.01)
*A61F 9/008* (2006.01)

(52) U.S. Cl.
CPC .............. *A61F 9/008* (2013.01); *A61B 90/30* (2016.02); *A61F 9/00736* (2013.01); *A61B 1/0057* (2013.01); *A61B 2090/306* (2016.02); *A61F 2240/00* (2013.01); *Y10T 29/49826* (2015.01)

(58) Field of Classification Search
CPC .. A61F 9/008; A61F 9/00736; A61F 2240/00; A61B 90/30; A61B 2090/306; A61B 1/0057; Y10T 29/49826; Y10T 29/49838; Y10T 29/49904; Y10T 29/49968; B23P 11/00; B23P 15/00; B23P 2700/00
USPC ........................................................ 606/2–19
See application file for complete search history.

(56) References Cited

U.S. PATENT DOCUMENTS

| 4,075,442 A * | 2/1978 | Fukuda .................. H01H 15/06 200/16 D |
| 4,858,810 A | 8/1989 | Intlekofer et al. |
| 4,941,455 A | 7/1990 | Chikama |
| 4,986,257 A | 1/1991 | Yu et al. |
| 5,281,214 A | 1/1994 | Wilkins et al. |

(Continued)

FOREIGN PATENT DOCUMENTS

| EP | 2074955 A2 | 7/2009 |
| EP | 2604174 | 6/2013 |

(Continued)

OTHER PUBLICATIONS

PCT/US2015/014197; International Search Report, International Searching Authority, dated Apr. 29, 2015, 2 pgs.

*Primary Examiner* — Christopher A Flory
*Assistant Examiner* — Wynn Huh

(57) ABSTRACT

A method of manufacturing an articulating ophthalmic surgical probe includes providing a cannula having an outer diameter of 20 Ga or less and a slotted tip, permanently attaching a pull wire to the slotted tip, permanently attaching a metal anchor to a distal end of the pull wire, positioning a weld pin within a handle assembly that is sized to fit within a single hand, and welding the metal anchor to the weld pin within the handle assembly.

15 Claims, 7 Drawing Sheets

(56) References Cited

U.S. PATENT DOCUMENTS

| | | |
|---|---|---|
| 5,344,424 A | 9/1994 | Roberts et al. |
| 5,365,928 A | 11/1994 | Rhinehart et al. |
| 5,397,304 A | 3/1995 | Truckai |
| 5,626,553 A | 5/1997 | Frassica et al. |
| 5,849,011 A | 12/1998 | Jones et al. |
| 6,554,794 B1 * | 4/2003 | Mueller ............. A61B 17/3478 604/528 |
| 6,984,230 B2 | 1/2006 | Scheller et al. |
| 2003/0023236 A1 * | 1/2003 | Gowda ................. A61B 18/24 606/15 |
| 2003/0120148 A1 * | 6/2003 | Pacetti ................. A61M 25/09 600/421 |
| 2009/0093800 A1 | 4/2009 | Auld et al. |
| 2010/0069790 A1 | 3/2010 | Green |
| 2011/0251554 A1 | 10/2011 | Romoscanu |
| 2012/0227746 A1 * | 9/2012 | Harrington ........... A61M 16/04 128/207.14 |
| 2013/0035551 A1 * | 2/2013 | Yu ........................ A61B 1/0057 600/141 |
| 2013/0226155 A1 | 8/2013 | Bookbinder et al. |
| 2013/0253387 A1 * | 9/2013 | Bonutti .............. A61H 23/0245 601/46 |

FOREIGN PATENT DOCUMENTS

| | | | |
|---|---|---|---|
| JP | 2001149307 A | | 6/2001 |
| JP | 2002272751 A | | 9/2002 |
| JP | 2005516636 A | | 6/2005 |
| JP | 2009101076 A | | 5/2009 |
| JP | 2009183718 A | * 8/2009 | ......... A61B 17/3211 |
| JP | 2009183718 A | | 8/2009 |

* cited by examiner

MANUFACTURING AN ARTICULATING OPHTHALMIC SURGICAL PROBE

This application claims the priority of U.S. Provisional Application No. 61/936,434 filed Feb. 6, 2014.

FIELD OF THE INVENTION

This invention relates to ophthalmic surgical equipment and more particularly to posterior segment ophthalmic surgical probes.

BACKGROUND OF THE INVENTION

Microsurgical instruments typically are used by surgeons for removal of tissue from delicate and restricted spaces in the human body, particularly in surgery on the eye, and more particularly in procedures for removal of the vitreous body, blood, scar tissue, or the crystalline lens. Such instruments include a control console and a surgical handpiece with which the surgeon dissects and removes the tissue. With respect to posterior segment surgery, the handpiece may be a vitreous cutter probe, a laser probe, or an ultrasonic fragmenter for cutting or fragmenting the tissue and is connected to the control console by a long air-pressure (pneumatic) line and/or power cable, optical cable, or flexible tubes for supplying an infusion fluid to the surgical site and for withdrawing or aspirating fluid and cut/fragmented tissue from the site. The cutting, infusion, and aspiration functions of the handpiece are controlled by the remote control console that not only provides power for the surgical handpiece(s) (e.g., a reciprocating or rotating cutting blade or an ultrasonically vibrated needle), but also controls the flow of infusion fluid and provides a source of vacuum (relative to atmosphere) for the aspiration of fluid and cut/fragmented tissue. The functions of the console are controlled manually by the surgeon, usually by means of a foot-operated switch or proportional control.

During posterior segment surgery, the surgeon typically uses several handpieces or instruments during the procedure. This procedure requires that these instruments be inserted into, and removed out of the incision. This repeated removal and insertion can cause trauma to the eye at the incision site. To address this concern, hubbed cannulae were developed at least by the mid-1980s. These devices consist of a narrow tube with an attached hub.

The tube is inserted into an incision in the eye up to the hub, which acts as a stop, preventing the tube from entering the eye completely. Surgical instruments can be inserted into the eye through the tube, and the tube protects the incision sidewall from repeated contact by the instruments. In addition, the surgeon can use the instrument, by manipulating the instrument when the instrument is inserted into the eye through the tube, to help position the eye during surgery.

Many surgical procedures require access to the sides or forward portion of the retina. In order to reach these areas, the surgical probes must be pre-bent or must be bendable intra-operatively. Various articulating optical surgical probes for providing laser and/or illumination light are known. See for example, U.S. Pat. No. 5,281,214 (Wilkins, et al.) and U.S. Pat. No. 6,984,130 (Scheller, et al.). The articulation mechanism, however, adds extra complexity and expense. One flexible laser probe needing no articulation mechanism is commercially available, but this device uses a relatively large diameter optical fiber sheathed in a flexible tube comprising the distal tip, resulting in a large bend radius and large distal tip diameter with significant bend stiffness. These characteristics require that the distal tip contain a non-bent straight portion for ease of insertion of the bent portion, which must flexibly straighten as it passes through the hubbed cannula. The straight portion of the distal tip allows the bent portion to flexibly pass through the hubbed cannula before the distal cannula of the handpiece enters the hubbed cannula, to allow maximum bending clearance of the flexible portion, thereby minimizing the bending strain and corresponding frictional insertion forces. Such a large bend radius, large diameter flexible tube, and straight distal tip causes the useable portion of the fiber to extend a relatively long distance from the distal tip of the probe and limits access of the probe.

A further disadvantage in the known art is the flexibility of the distal cannula, which is a function of the material properties and cross sectional moment of inertia, as determined by the gauge size of the outside diameter of the cannula to fit within the hubbed cannula, and the inside diameter of the cannula to accept the flexible tube. For any given material, the outer and inner diameters of the cannula determine the flexibility of the cannula. This flexibility limits the surgeon's ability to use the instrument to manipulate the position of the eye during surgery.

A flexible-tip probe is disclosed in U.S. Patent Application Publication 2009/0093800 (Auld, et al.) that does not require a straight portion of flexible tube, which thus provides a more compact useable tip length, thereby allowing greater access to internal posterior structures of the eye without compromising insertion forces. The flexible-tip probe provides increased rigidity of the distal cannula to facilitate manipulation of the position in the eye during surgery. While this probe provides a relatively smaller cross section as compared to the previous probes, such as those disclosed by Scheller et al., it does not provide controllable articulation over a range of angles in the manner those probes do.

A more recent approach described in U.S. Patent Application Publication 2013/0035551 (Auld, et al.), which is incorporated herein by reference, discloses a single cannula with a flexible tip that is articulable using a pull-wire. This combines the advantages of a very small diameter with controllable articulation of the probe tip. This approach combines advantages of other previous alternatives and provides a simple alternative. Any improvements to the ability to manufacture such probes with increased ease and reliability would therefore be valuable.

BRIEF SUMMARY OF THE INVENTION

In particular embodiments of the present invention, an articulating ophthalmic surgical probe includes a handle formed from a rigid plastic material and sized to fit in a single hand, a rigid cannula extending from the handle having a diameter of 20 Ga or less, and a slotted tip at a distal end of the cannula. The probe further includes at least one optical fiber extending through the handle, the single rigid cannula, and the slotted tip. A pull-wire is permanently attached to the slotted tip, When the pull-wire exerts tension on the slotted tip, the slotted tip will deviate from straight to a bend angle controlled by the tension in the pull-wire, and the slotted tip is formed from a resilient material that will restore to the straight position when the tension exerted by the pull-wire is released. The probe further includes an anchor permanently attached to a distal end of the pull wire, and a weld pin secured within the handle welded to the anchor.

In other embodiments, a method of manufacturing an articulating ophthalmic surgical probe includes providing a cannula having an outer diameter of 20 Ga or less and a slotted tip, permanently attaching a pull wire to the slotted tip, permanently attaching a metal anchor to a distal end of the pull wire, positioning a weld pin within a handle assembly that is sized to fit within a single hand, and welding the metal anchor to the weld pin within the handle assembly.

Other objectives, features and advantages of the present invention will become apparent with reference to the drawings, and the following description of the drawings and claims.

DETAILED DESCRIPTION OF THE INVENTION

Various embodiments of the present invention may allow improved reliability and simplicity in the manufacture of articulating ophthalmic surgical probes. Articulating ophthalmic surgical probes with a single rigid cannula having a slotted tip of resilient material secured to a pull wire have been described in U.S. Patent Application Publication 2013/0035551. Tension in the pull wire causes the slotted tip to bend in a particular direction, while releasing the tension allows the resilient tip to restore to its straight position. Pull-wire technology has been used previously to deviate a distal end of a surgical catheter, but not in a small-diameter, rigid cannula used in handheld optical surgical probes nor with the degree of angular movement used in the relatively small spaces found within the interior of an eye. Consequently, the application of pull-wire tension in the context of hand-held surgical probes is uniquely advantageous.

Such probes can be manufactured by the use of adhesives or similar assembly techniques to connect metal parts of the probe (including the pull wire and cannula) to a plastic housing. Particularly given the small components and relatively small contact are between them, the strength of the adhesive bond may be highly variable. In particular, factors such as inconsistent application, surface contamination, heat, moisture, or age may cause the adhesive bonds to fail. Additionally, given the small scale of the components and the relatively stringent manufacturing tolerances required combined with the additional requirements of alignment so that the probe can articulate in the correct direction, even aligning the components of the probe is relatively challenging. Various embodiments of the present invention provide improvements in manufacturing processes for an articulating ophthalmic surgical probe that uses a pull wire for articulation.

Figure 1:
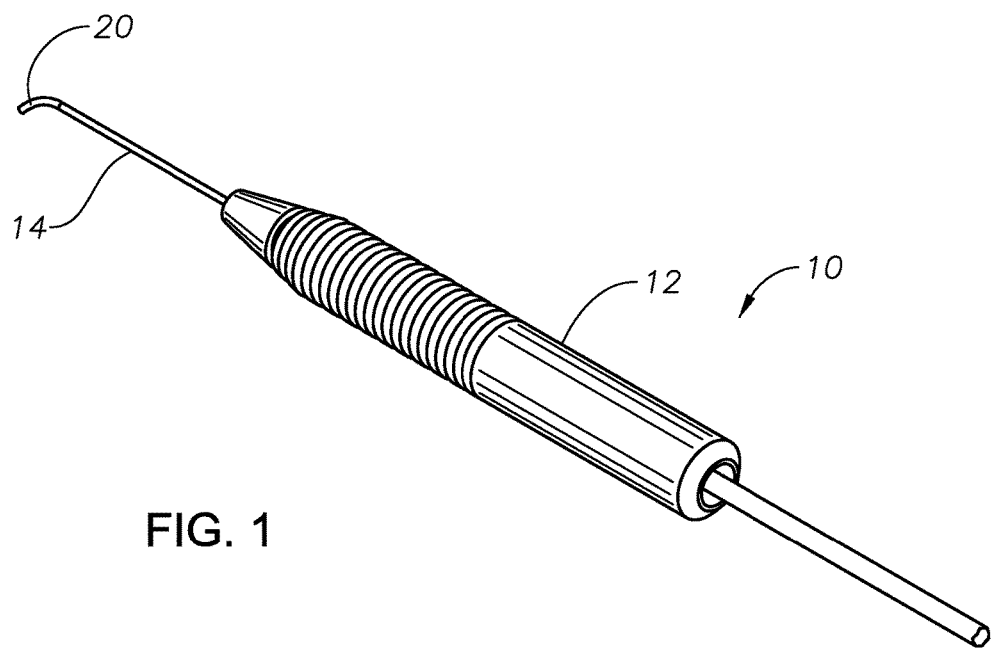
FIG. 1 is a schematic of an articulating optical surgical endoprobe, according to a particular embodiment of the present invention.

FIG. 1 is a schematic of an articulating optical surgical endoprobe 10, according to a particular embodiment of the present invention, with a handle 12 suitable for being held in a single hand and a cannula 14. (For ease of illustration, the handle 12 and cannula 14 are not shown to scale and certain external features of the handle 12, such as the control mechanism for an internal pull-wire, are not shown.) The handle 12 is formed of one or more rigid plastic materials, such as acrylonitrile butadiene styrene (ABS), acetal homopolymer, or polypropylene. The proximal end of the endoprobe 10 is connected to one or more light sources (not shown) that provide laser and/or illumination light by connection to at least one optical fiber running through the interior of the endoprobe 10. The cannula 14 is formed of a rigid biocompatible metal, such as stainless steel. The cannula 14 has a slotted tip 20 at a distal end (referring to the end farthest from the surgeon during use). The slotted tip 20 may articulate in a selected direction in a controllable manner by applying tension to a pull wire secured within the slotted tip 20 (not shown in FIG. 1).

The metal components of the probe 10 (namely, the pull wire and the cannula) can be attached to one another by welding, and given the high precision required, this preferably would use laser welding. This can be used to attach the pull wire to the cannula, for example. Metal weld points, such as stainless steel pins, can be molded, inserted or otherwise positioned in the plastic handle 12 so that the pull wire can also welded to the handle 12. But the pull wire has such a narrow diameter (0.004 inches or less) that the increased heat from the welding can cause the wire to break if it is under significant tension. Thus, the pull wire could be broken if it is welded while it is threaded within the housing in the correct position to be able to exert tension on the flexible tip, so the secure attachment of the pull wire within the handle 12 may remain problematic.

Figure 2:
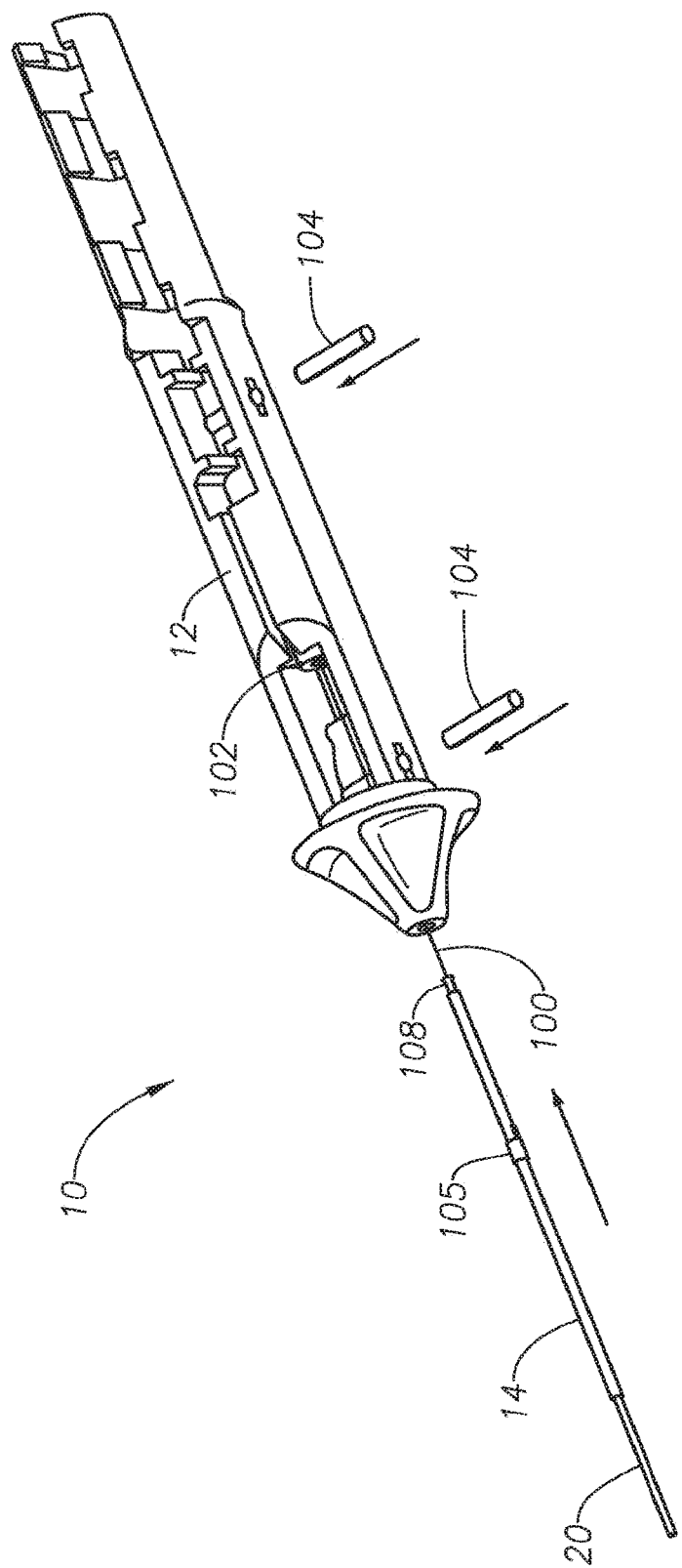
FIG. 2 illustrates a pull wire, cannula and handle assembly and weld pins according to a particular embodiment of the present invention.

FIG. 2 illustrates an exploded view of a probe 10 with a pull wire 100 coupled to cannula 14 which advantageously resolves this problem according to a particular embodiment of the present invention. The pull wire 100, which has a diameter of 0.004 inches or less, is permanently attached to a metal anchor 102 (not shown), preferably by laser welding (where "permanently attached" in this specification refers to two components are joined by a physical bond that can be broken only by damage or destruction of the bond). The metal anchor 102 may be formed from any suitable metal, including stainless steel. The pull wire 100 is likewise permanently attached, preferably by laser welding, to the inside of the cannula 14 at the slotted tip 20, which will allow the pull wire 100 to exert tension to bend the slotted tip 20 when the probe 10 is fully assembled.

The anchor 102 is welded to a weld pin 104 within the housing (not shown). A distal weld pin 104' is used for the cannula 14. The weld pins 104, 104' may include any fixed metal piece that is held securely in the handle 12 when welded to the respective component (anchor 102 or cannula 14), and the weld pins 104, 104' need not be the same shape or size. In a particular example, the weld pins 104, 104' may include U-shaped grooves on an end or side of the weld pin 104, 104' so that the anchor 102 or cannula 14 fits within the U-shaped groove of the respective weld pin 104, 104' for welding (not shown). Although U-shaped grooves can be advantageous for cylindrical symmetry of the cannula 14 and anchor 102, other shapes could also be used, including different grooves (for example, V-shaped or rectangular grooves), flat surfaces, rails, or other features to facilitate secured welds to the weld pins 104, 104'. In an alternative example, the weld pins 104, 104' may be ends of an integral assembly, such as a support wire, that is held securely in the handle 12 after welding (not shown). Such an assembly can act as a heat sink to remove heat from the weld pins 104, 104' in order to reduce the possibility of damage to the plastic handle 12. In other embodiments, a separate heat sink, such as a metal rod, can be placed in contact with the weld pin 104, ψ' anchor 102 or cannula 14 during welding to conduct heat away from the weld pin 104, 104'.

Figure 3:
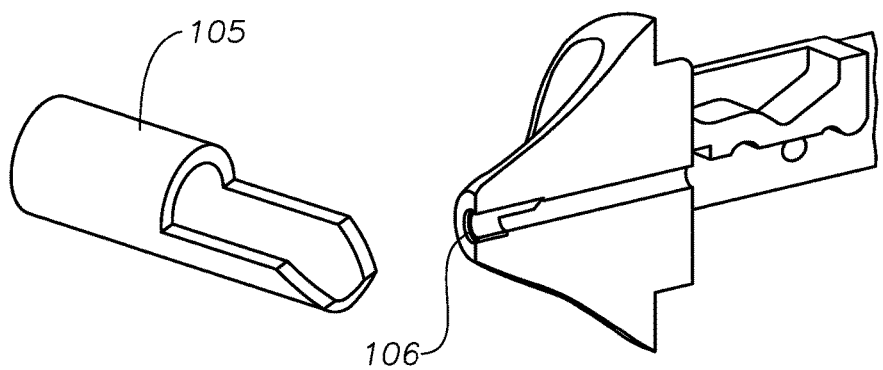
FIG. 3 illustrates a key feature and keypath pocket of a handle assembly according to a particular embodiment of the present invention.

The cannula 14 likewise has additional features that facilitate assembly of the probe 10. Specifically, the cannula 14 has a key feature 105 permanently attached to an exterior of the cannula 14. As shown in FIG. 3, the key feature 105 is an asymmetrical structure extending away from the cannula that fits into a matching keyway pocket 106 at a distal end of the plastic handle 12 ("distal" referring to the end of the handle 12 that would face away from the surgeon during use, as opposed to "proximal"). The key feature can be part of a sleeve permanently attached to the cannula 14, or it may be directly attached to the cannula 14.

During assembly of the probe 10, the cannula 14 slides into the distal end of the handle 12 until the key feature 105 reaches the keyway pocket 106. The asymmetry of the key feature 105 assures correct rotational alignment of the cannula 14, so that the slotted tip 20 articulates in the correct direction. The key feature 105 also acts as a stop to prevent further movement of the cannula 14 once the key feature 105 reaches the keyway pocket 106, assuring correct axial positioning of the cannula 14 within the handle 12.

Figure 4A:
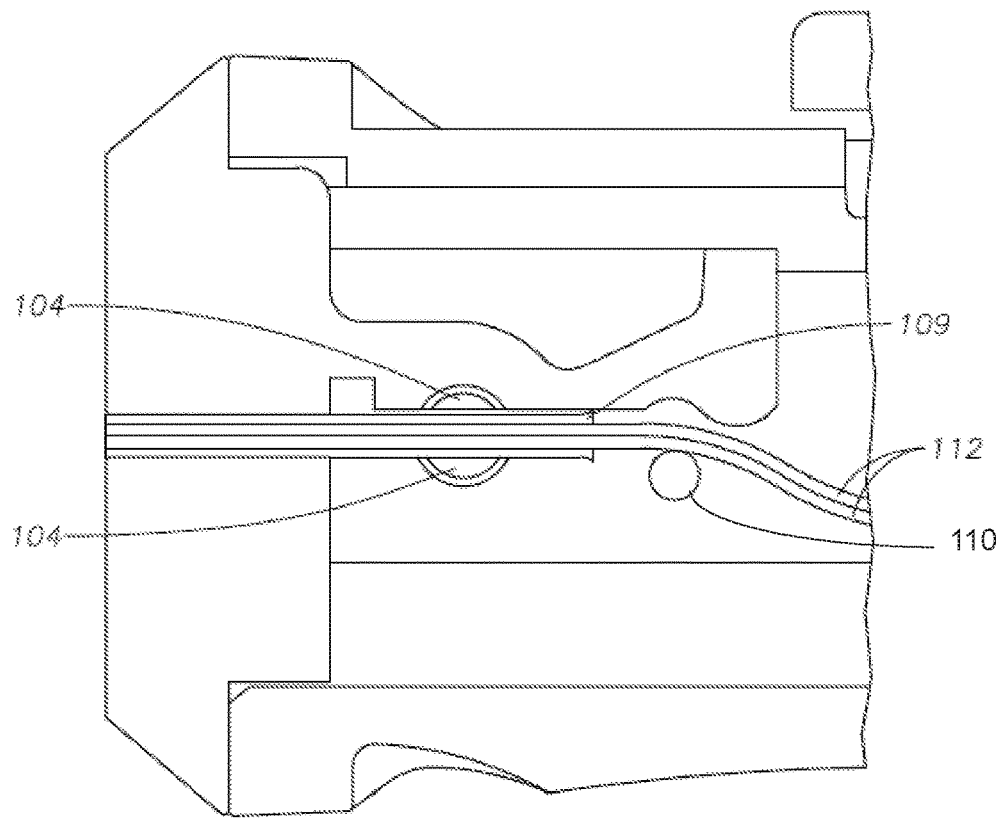
FIGS. 4A and 4B illustrate a cannula with a flared proximal end according to a particular embodiment of the present invention.
Figure 4B:
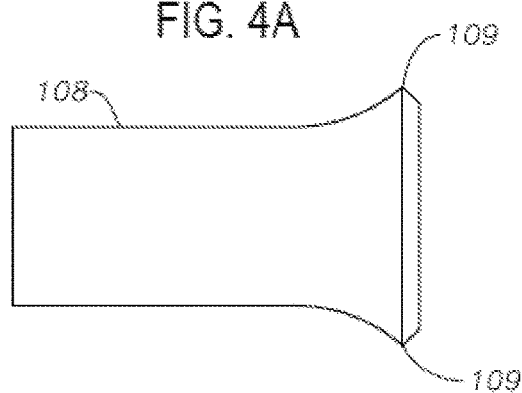

As shown in FIGS. 4A and 4B, the cannula 14 also includes a flared proximal end 108, which is shown in greater detail in the magnified view of FIG. 4B. The flared proximal end 108 is placed relative to a guide pin 110 within the handle 12 over which one or more optical fibers 112 within the handle 12 that hold the optical fibers 112 in place. In particular, the optical fibers 112 are held away from an outer edge 109 of the flared proximal end 108 when positioned over the guide pin 110. This prevents the optical fibers 112 from contacting the corner of the cannula 14, which could cause the optical fibers 112 to be nicked or broken. Additionally, the guide pin 110 is placed at a sufficient distance from the flared proximal end 108 to prevent the optical fibers 112 from bending with a bend radius less than a minimum critical radius (i.e., the bend radius at which the fiber will be unable to properly transmit light and/or will be damaged). For small-gauge single-mode laser fibers (0.004 inch diameter) and multimode illumination fibers (0.007 inch diameter), the minimum bend radius may be around 0.193 inches. Given conventional dimensions for a handheld probe 10 and suitable placement of the light source connector near the proximal end of the handle 12, the bend radius can be kept above 0.690 inches by the guide pin 110, which provides a significant safety margin for small-gauge optical fibers 112.

Figure 5:
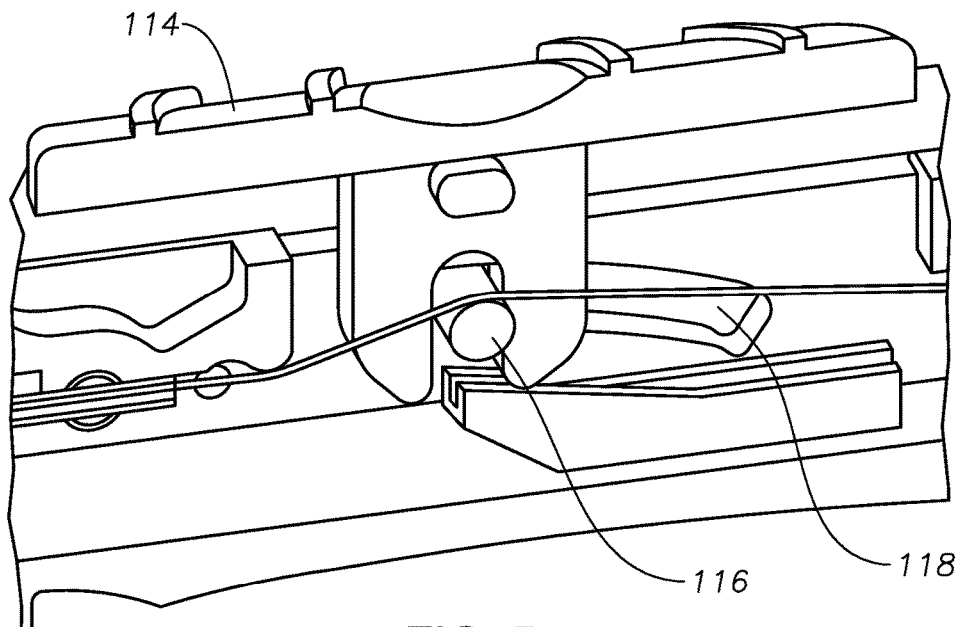
FIGS. 5 and 6 illustrate a thumb switch for adjusting tension in a pull wire according to a particular embodiment of the present invention.
Figure 6:
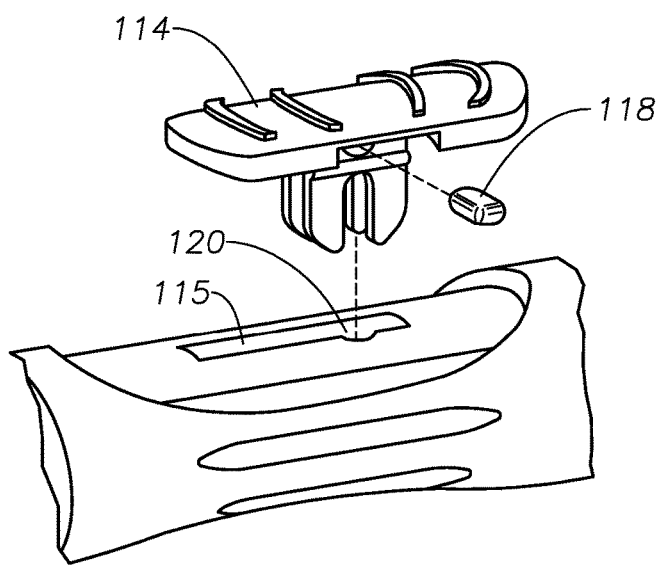

FIGS. 5 and 6 illustrate a tension mechanism for the pull wire according to a particular embodiment of the present invention. In the depicted embodiment, a thumb switch 114 is used to advance a slider pin 116 along a ramp 118 to adjust tension in the pull wire 100, causing the slotted tip 20 to articulate to an angled position. The thumb switch 114 is snap fit into a slot 115 in the handle 12, allowing the switch 114 to slide. Due to manufacturing tolerances, there may be slight variations in the fit of the switch 114 within the slot. This may result in variability of the force required to advance the switch 114 and thus to articulate the slotted tip 20. Therefore, a compressible insert 130 is placed in the switch 114 that contacts the slot, providing a uniform frictional force. Preferably, this material is a low-friction silicone, so that the force required to advance the switch 114 is low but uniform.

The slot 115 in the handle 12 includes a widened portion 120 corresponding to the position of the compressible insert 130 when the switch 114 is in its rearmost (i.e., farthest proximal) position. This allows the compressible insert 130 to expand so as to retain the switch 114 in this rearmost position until the probe 10 is used, which reduces the chance of the switch 114 advancing during storage or transport.

Figure 7:
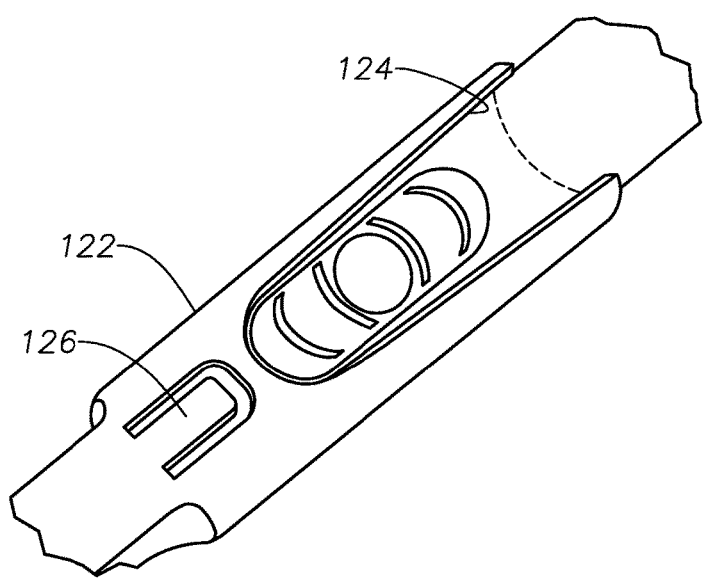
FIG. 7 illustrates a protective cover with a thumb switch according to a particular embodiment of the present invention.

FIG. 7 illustrates a protective cover 122 that also helps to maintain the switch 114 in the rearmost position. In the depicted embodiment, the protective cover 122 includes a tapered slot 124, which reduces any drag on the switch 114 due to friction when the protective cover 122 is removed. The protective cover 122 is held in place by retention tabs 126.

Figure 8A:
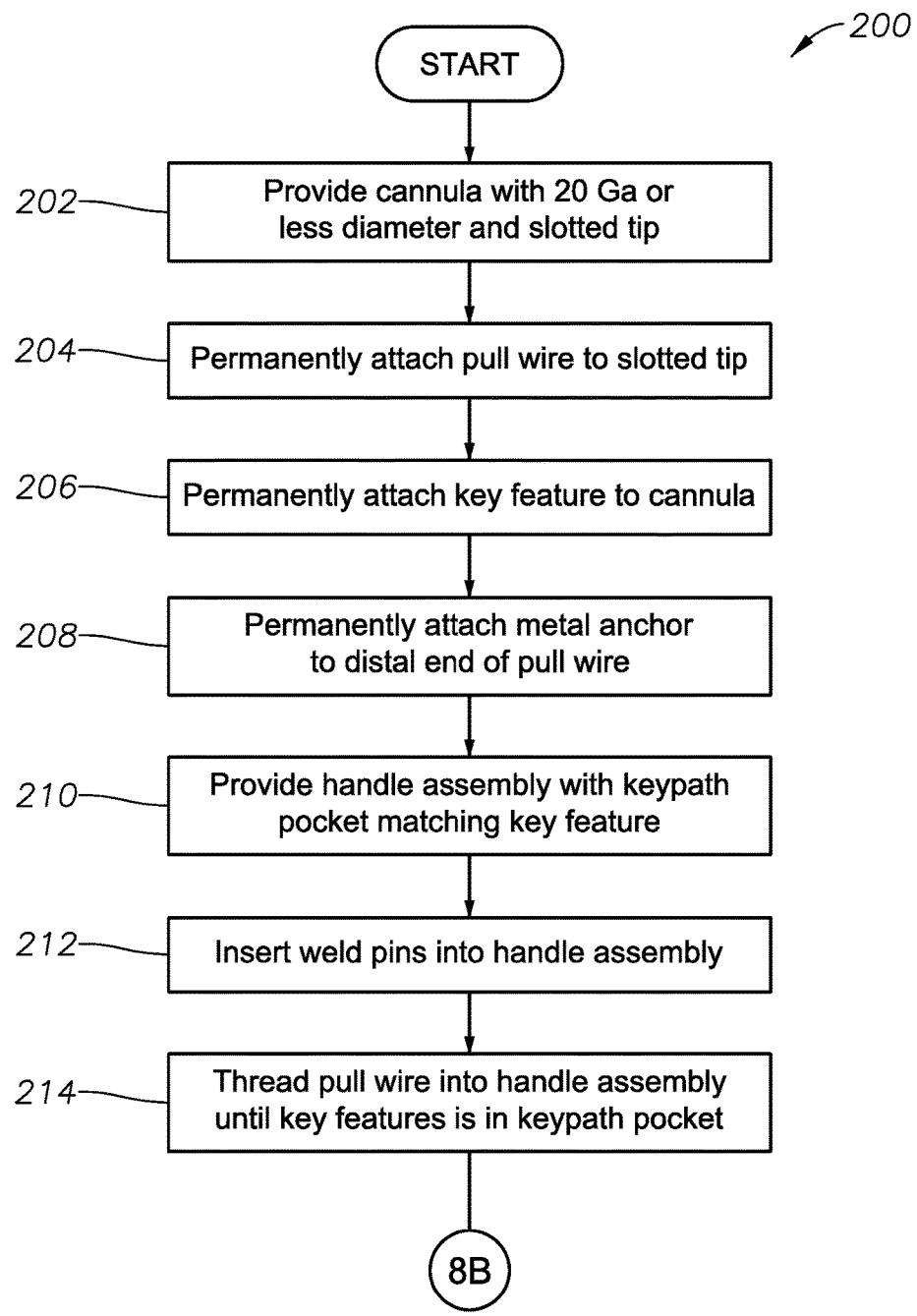
FIGS. 8A and 8B show a flow chart illustrating an example method for assembling an articulating ophthalmic surgical probe according to a particular embodiment of the present invention.
Figure 8B:
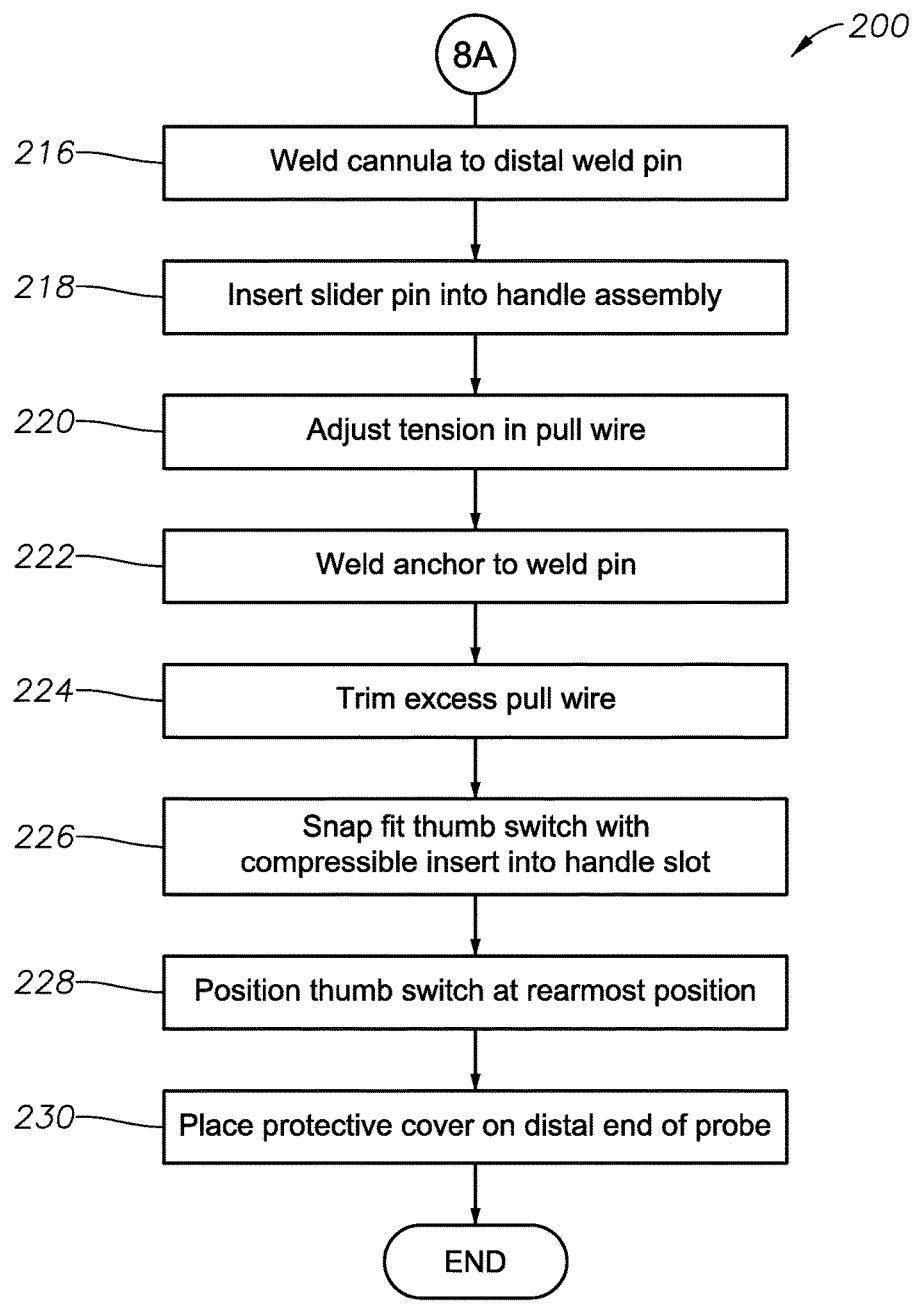

FIGS. 8A and 8B show a flow chart 200 illustrating an example method for manufacturing a probe 20 according to a particular embodiment of the present invention. At step 202, a cannula with a diameter of 20 Ga or less having a slotted tip is provided. At step 204, a pull wire is permanently bonded to the slotted tip, such as by laser welding, so as to allow the tip to articulate when tension on the pull wire is increased. At step 206, a key feature is permanently attached to the cannula. Then, at step 208, a metal anchor is permanently bonded to the pull wire, such as by laser welding. Steps 202-208 form the cannula assembly that will be welded to the handle assembly in forming the probe.

At step 210, a handle assembly is provided. The handle assembly has a keypath pocket at a distal end matching the key feature. At step 212, weld pins are inserted into the handle assembly. At step 214, the pull wire is threaded into the handle assembly until the key features fits into the keypath pocket. The cannula is welded to a distal weld pin at step 216.

At steps 218-224, the tension in the pull wire is adjusted to produce the correct bend in the slotted tip of the cannula. At step 218, a slider pin is inserted into a ramp of the handle assembly. At step 220, the tension in the pull wire is adjusted to produce a calibrated bend in the slotted tip. The anchor on the pull wire is then welded to the proximal weld pin at step 222. Any excess pull wire may be trimmed away at step 224.

At step 226, a thumb switch is snap fit into a slot in the handle assembly, where it fits onto the slider pin. The thumb switch is placed into a rearmost position at step 228, where a compressible insert in the thumb switch expands into a widened portion of the slot to retain the thumb switch in the rearmost position. A protective cover is placed onto a distal end of the probe at step 228, which also is configured to retain the thumb switch in the rearmost position.

While certain embodiments of the present invention have been described above, these descriptions are given for purposes of illustration and explanation. Variations, changes, modifications and departures from the systems and methods disclosed above that would be apparent to one skilled in the art may be adopted without departure from the scope of the present invention as recited in the following claims.

What is claimed is:

1. An articulating ophthalmic surgical probe, comprising:
a handle formed from a rigid plastic material and sized to fit in a single hand;
a rigid cannula extending from the handle having a diameter of 20 Ga or less;
a slotted tip at a distal end of the cannula;
at least one optical fiber extending through the handle, the single rigid cannula, and the slotted tip;
a pull-wire permanently attached to the slotted tip at a distal end of the pull-wire, wherein when the pull-wire exerts tension on the slotted tip, the slotted tip will deviate from a straight position to a bent position controlled by the tension in the pull-wire, the slotted tip formed from a resilient material that will restore to the straight position when the tension exerted by the pull-wire is released;
an anchor permanently attached to a proximal end of the pull wire;
a proximal weld pin secured within the handle coupled with the anchor; and
a sliding pin located within the handle, wherein, when the sliding pin is in a first position, the sliding pin does not deflect the pull-wire from the substantially straight orientation, and
a slot in the handle, the slot including a widened portion; and
a switch coupled within the slot, the switch configured to slide relative to the handle and engage with the sliding pin and, when slid towards the slotted tip, configured to advance the sliding pin from the first position to an additional position, causing a deflection of the pull-wire and an associated increase in the tension of the pull-wire, the increased tension causing the slotted tip to deviate from a straight position to a bent position,
the switch further comprising a compressible insert which:
aligns with the widened portion of the slot when the switch is in the first position, and
interfaces with a wall of the slot such that when the switch is in an additional position in the slot, such that, when the compressible insert is slid past the widened portion of the slot and slid through the slot along with the switch, the compressible insert provides a uniform frictional force on the handle.

2. The probe of claim 1, further comprising:
a key feature permanently attached to the rigid cannula; and
a keypath pocket holding the key feature to align the slotted tip rotationally with the handle.

3. The probe of claim 1, wherein:
the rigid cannula has a flared proximal end;
the handle further comprises a guide pin spaced from the flared proximal end of the rigid cannula contacting the at least one optical fiber, wherein the guide pin holds the at least one optical fiber away from an outer edge of the flared proximal end.

4. The probe of claim 1, further comprising:
a distal weld pin welded to the cannula.

5. The probe of claim 4, wherein the proximal weld pin and the distal weld pin are formed in an integral assembly comprising the proximal weld pin and the distal weld pin as ends of a support wire that is held within the handle, wherein the support wire acts as a heat sink when the distal weld pin and the proximal weld pin are welded to the cannula and the anchor, respectively.

6. The probe of claim 1, wherein one or more of the proximal weld pin and the distal weld pin are formed of stainless steel.

7. The probe of claim 1, wherein:
the anchor is a cylindrical anchor having an outer diameter; and
the proximal weld pin has a U-groove having an internal diameter larger than the outer diameter of the anchor so that the anchor fits within a bottom of the U-groove.

8. The probe of claim 1, wherein the rigid plastic material is acrylonitrile butadiene styrene (ABS), acetal homopolymer, or polypropylene.

9. The probe of claim 1, wherein the cannula is formed of stainless steel.

10. The probe of claim 1, wherein the pull wire is formed of stainless steel.

11. A method of manufacturing an articulating ophthalmic surgical probe, comprising:
providing a cannula having an outer diameter of 20 Ga or less and a slotted tip;
permanently attaching a pull wire to the slotted tip;
permanently attaching a metal anchor to a distal end of the pull wire;
positioning a proximal weld pin within a handle assembly, the handle assembly sized to fit within a single hand, the handle further including:
a sliding pin located within the handle, wherein, when the sliding pin is in a first position, the sliding pin does not deflect the pull-wire from the substantially straight orientation,
a slot in the handle, the slot including a widened portion;
coupling the metal anchor to the proximal weld pin within the handle assembly; and
inserting a switch within the slot, the switch configured to slide relative to the handle and engage with the sliding pin and, when slid towards the slotted tip, configured to advance the sliding pin from the first position to an additional position, causing a deflection of the pull-wire and an associated increase in the tension of the pull-wire, the increased tension causing the slotted tip to deviate from a straight position to a bent position, the switch further comprising a compressible insert which: aligns with the widened portion of the slot when the switch is in the first position, and, interfaces with a wall of the slot such that when the switch is in an additional position in the slot, such that, when the compressible insert is slid past the widened portion of the slot and slid through the slot along with the switch, the compressible insert provides a uniform frictional force on the handle.

12. The method of claim 11, wherein:
the handle assembly further comprises a keypath pocket at a distal end of the handle assembly; and
the method further comprises:
permanently attaching a key feature to the cannula; and
threading the pull wire through the distal end of the handle assembly until the key feature fits with the keypath pocket to rotationally align the slotted tip relative to the handle assembly.

13. The method of claim 11, further comprising:
positioning a distal weld pin within the handle assembly; and
welding the cannula to the distal weld pin within the handle assembly.

14. The method of claim 11, wherein the step of welding the metal anchor is performed using laser welding.

15. The method of claim 11,
wherein the switch is a thumb switch, and
wherein the method further comprises placing the thumb switch in the first position to allow the compressible insert to expand into the widened portion of the slot, thereby retaining the thumb switch in the first position.

\* \* \* \* \*